(12) United States Patent
Schmidt et al.

(10) Patent No.: US 10,031,080 B2
(45) Date of Patent: Jul. 24, 2018

(54) METHOD FOR RECOGNIZING RESISTANT GERMS AND DEVICE FOR PERFORMING SAME

(71) Applicants: Fraunhofer-Gesellschaft Zur Forderung Der Angewandten Forschung E.V., Munich (DE); Asklepios Kliniken Verwaltungsgesellschaft mbH, Konigstein (DE)

(72) Inventors: Jennifer Schmidt, Falkenstein (DE); Ignaz Eisele, Icking (DE); Sabine Trupp, Saalfeld (DE); Karl Haberger, Martinsried (DE); Wolfgang Sittel, Bad Homburg (DE)

(73) Assignees: Fraunhofer-Gesellschaft zur Förderung der angewandten Forschung e.V. (DE); Asklepios Kliniken Verwaltungsgesellschaft mbH (DE)

( * ) Notice: Subject to any disclaimer, the term of this patent is extended or adjusted under 35 U.S.C. 154(b) by 139 days.

(21) Appl. No.: 15/172,386

(22) Filed: Jun. 3, 2016

(65) Prior Publication Data

US 2016/0282269 A1 Sep. 29, 2016

Related U.S. Application Data

(63) Continuation of application No. PCT/EP2014/076362, filed on Dec. 3, 2014.

(30) Foreign Application Priority Data

Dec. 5, 2013 (DE) ........................ 10 2013 225 037

(51) Int. Cl.
*G01N 21/64* (2006.01)
*C12Q 1/04* (2006.01)
(Continued)

(52) U.S. Cl.
CPC ........... *G01N 21/6428* (2013.01); *C12Q 1/04* (2013.01); *C12Q 1/18* (2013.01); *G01N 21/6486* (2013.01);
(Continued)

(58) Field of Classification Search
CPC .... C12Q 1/04; C12Q 1/18; G01N 2021/6439; G01N 21/64; G01N 21/6428;
(Continued)

(56) References Cited

U.S. PATENT DOCUMENTS 3,509,026 A 4/1970 Sanders
3,925,166 A 12/1975 Blume
(Continued)

FOREIGN PATENT DOCUMENTS

DE 3327839 A1 2/1985
DE 19945553 B4 3/2001
(Continued)

OTHER PUBLICATIONS

Tsou et al. Biosensors and Bioelectronics, vol. 26, Jul. 1, 2010, pp. 289-294.*
(Continued)

*Primary Examiner* — Maureen Wallenhorst
(74) *Attorney, Agent, or Firm* — Haynes and Boone, LLP (57) ABSTRACT

A method for detecting resistant germs in a sample includes contacting the sample by a sample carrier which has an agent for killing different germs. In addition, the method includes introducing the sample carrier into an analyzer and detecting light emissions from the sample carrier by the analyzer. An indication is output by the analyzer indicating that the sample contains at least one germ resistant to the agent for killing different germs, if the light emission exceeds a threshold value, or indicating that the sample does not contain germs resistant to the agent for killing different
(Continued)

germs, if the light emission does not exceed the threshold value.

15 Claims, 3 Drawing Sheets (51) Int. Cl.
C12Q 1/18 (2006.01)
G01N 33/569 (2006.01)

(52) U.S. Cl.
CPC ... *G01N 33/569* (2013.01); *G01N 2021/6439* (2013.01); *G01N 2201/0221* (2013.01); *G01N 2201/061* (2013.01)

(58) Field of Classification Search
CPC ....... G01N 21/6486; G01N 2201/0221; G01N 2201/061; G01N 33/569
USPC ......... 436/147, 164, 169, 172; 422/400–404, 422/411, 420, 82.05, 82.08, 82.09; 435/4, 435/5, 29, 30, 32, 34, 39, 252.1
See application file for complete search history.

(56) References Cited

U.S. PATENT DOCUMENTS

| 4,622,297 | A | 11/1986 | Kappner | |
|---|---|---|---|---|
| 5,702,684 | A | 12/1997 | McCoy | |
| 6,140,069 | A | 10/2000 | Wardlaw | |
| 6,750,038 | B1 | 6/2004 | Nakane | |
| 2005/0003346 | A1* | 1/2005 | Voorhees | C12Q 1/04 435/5 |
| 2005/0202523 | A1* | 9/2005 | Shaw | C12O 1/06 435/34 |
| 2009/0136953 | A1* | 5/2009 | Gold | C12O 1/18 435/5 |
| 2013/0217063 | A1* | 8/2013 | Metzger | C12Q 1/04 435/32 |

FOREIGN PATENT DOCUMENTS

| DE | 69934789 T2 | 10/2007 |
|---|---|---|
| EP | 0054001 A1 | 6/1982 |
| EP | 0174477 A1 | 3/1986 |
| GB | 1535643 A | 12/1978 |
| GB | 2233760 A | 1/1991 |
| WO | WO 8605206 A1 | 9/1986 |
| WO | WO 8904372 A1 | 4/1989 |
| WO | WO 9918232 A1 | 4/1999 |
| WO | WO 9945095 A1 | 9/1999 |
| WO | WO 2006077586 A2 | 7/2006 |
| WO | WO 2006092629 A1 | 9/2006 |
| WO | 2008/064241 * | 5/2008 |
| WO | WO 2010129779 A1 | 11/2010 |

OTHER PUBLICATIONS

Kayser F. H., K. A. Bienz, J. Eckert, R. M. Zinkernagel; Medizinische Mikrobiologie; Georg Thieme-Verlag, Stuttgart—New York (1998) 9. Auflage.

Brandis H., W. Köhler, H. J. Eggers, G. Pulverer; Lehrbuch der medizinischen Mikrobiologie; Gustav Fischer Verlag, Stuttgart—Jena—New York (1994) 7. Auflage.

Hallmann L. und F. Burkhardt, Klinische Mikrobiologie, Georg Thieme-Verlag, Stuttgart (1974) 4. Auflage.

Holfelder M., U. Eigner, A. Turnwald-Maschler, W. White, M. Weizenegger and A. M. Fahr,; Direct detection of methicillin-resistant *Staphylococcus aureus* in clinical specimens by a nucleic acid-based hyhridization assay; Clinical Microbiology and Infectious Diseases (May 2006) 12(12): 1163-1167.

Reischl U. and T. Holzmann; Aktuelle Verfahren zum Nukleinsäure geschützten Direktnachweis von MRSA; J Lab Med (2008) 32(4): 253-265.

Warren D. K., R. S. Liao, L. R. Merz, W. M. Jr. Dunne; Detection of methicillin-resistant *Staphylococcus aureus* directly from nasal swab specimens by a real time PCR assay; Journal of Clinical Microbiology (Aug. 2004) 42(12): 5578-5581.

www.microphage.com; MicroPhage opens clinical trial on microphage-based platform to identify MRSA. (Sep. 2009).

www.pcds-gmbh.de; Das Prinzip: Detektion von Immunkomplexen (PCDS Preventive Clinical Diagnostic Solutions).

Monis P.T., S. Giglio, C.P. Saint; Comparison of SYT09 and SYBR Green I for real-time polymerase chain reaction and investigation of the effect of dye concentration on amplification of DNA melting curve analysis; Analytical Biochemistry (2005) 340: 24-34.

Wlodkowic D., J. Skommer, Z. Darzynkiewicz; SYTO probes in the Cytometry of Tumor Cell Death; Cytometry A (Jan. 2008) 73: 496-507.

Wojcik K. and J. W. Dobrucki; Interaction of a DNA Intercalator DRAQ5, and a minor groove hinder SYTOJ7, with chromatin in live cells—influence on chromatin organization and histone-DNA interactions; Cytometry A (Mar. 2008) 73: 555-562.

Decker E. M.; The ability of direct fluorescence-based, two-colour assays to detect different physiological states of oral streptococci; Letters in Applied Microbiology (May 2001) 33: 188-192.

Leeder J. S., H. M. Dosch, P. A. Harper, P. Lam, S.P. Spielberg; Fluorescence-based viability assay for studies of reactive drug intermediates; Analytical Biochemistry (Sep. 1989) 177: 364-372.

Liminga G., B. Jonsson, P. Nygren, R. Larsson; On the mechanism underlying calcein-induced cytotoxicity; European Journal of Pharmacology (Sep. 1999) 383: 321-329.

Parthuisot N., P. Catala, K. Lemarchand, J. Baudart, P. Lebaron; Evaluation of ChemChrome V6 for bacterial viability assessment in waters; Journal of Applied Microbiology (Apr. 2000) 89: 370-380.

Eisenschmidt K., T. Lanio, A. Jeltsch, A. Pingoud; A fluorimetric assay for on-line detection of DNA cleavage by restriction endonucleases; Journal of Biotechnology (2002) 96: 185-191.

Ghosh S. S., P. S. Eis, K. Blumeyer, K. Fearon, D. P. Millar; Real time kinetics of restriction endonuclease cleavage monitored by fluorescence resonance energy transfer; Nucleic Acids Research (Jun. 1994) vol. 22, No. 15, 3155-3159.

Fudala R., M. E. Mummert, Z. Gryczynski, I. Gryczynski; Fluorescence detection of hyaluronidase; J Photochem Photobiol B (Sep. 2011) 104(3):473-477.

Fudala R., M. E. Mummert, Z. Gryczynski, R. Rich, J. Borejdo, I. Gryczynski; Lifetime-based sensing of the hyaluronidase using fluorescein labeled hyaluronic acid; J Photochem Photobiol B (Jan. 2012) 106(1): 69-73.

Zhang L. S. and M. E. Mummert; Development of a fluorescent substrate to measure hyaluronidase activity; Anal Biochem (Aug. 2008) 379(1): 80-85.

Peak E., I. W. Chalmers, K. F. Hoffmann; Development and validation of a quantitative, high-throughput, fluorescence-based bioassay to detect schistosoma viability; PLOS Neglected Tropical Diseases (Jul. 2010) vol. 4, Issue 7, e759.

Guilbault G. G. and D. N. Kramer; Fluorimetric procedure for measuring the activity of dehydrogenasis; Analytical Chemistry (Sep. 1965) vol. 37, No. 10, 1219-1221.

Rodriguez G. G., D. Phipps, K. Ishiguro, H. F. Ridgway; Use of a fluorescent redox probe for direct visualization of actively respiring bacteria; Applied and Environonmental Microbiology (Mar. 1992), vol. 58, No. 6, 1801-1808.

* cited by examiner

METHOD FOR RECOGNIZING RESISTANT GERMS AND DEVICE FOR PERFORMING SAME

CROSS-REFERENCE TO RELATED APPLICATIONS

This application is a continuation of copending International Application No. PCT/EP2014/076362, filed Dec. 3, 2014, which is incorporated herein by reference in its entirety, and additionally claims priority from German Application No. 10 2013 225 037.1, filed Dec. 5, 2013, which is also incorporated herein by reference in its entirety.

BACKGROUND OF THE INVENTION

The invention relates to a method for recognizing resistant germs in a sample material and to a device for performing the method.

A plurality of different bacteria are among the physiological flora of the skin and mucus membranes and thus part of the microbiome, i.e. the entirety of all the microorganisms populating the human body. In populating the human body, the bacteria perform important tasks, such as, for example, protecting the skin and the entire organism from pathogenic germs, i.e. germs dangerous to health, penetrating, since these compete for their habitat, i.e. the human body. When this system loses its balance, for example by a weak immune system, infections may result. Usually, infections caused by bacteria are easy and quick to treat by administering antibiotics.

However, over the years, the pathogens have developed resistances to the active substances used, thereby making therapy considerably more difficult. Germs and pathogens resistant to the active substances used are referred to as multi-resistant pathogens (MRP). This is a big problem in particular in hospitals and in nursing homes, since this is where old and sick people are, whose immune system is weakened and who, consequently, are particularly susceptible to infections. In addition, babies whose immune systems have not yet formed completely and immunosuppressed patients, like those in an intensive care unit, the immune of whom is suppressed by drugs, for example after transplants for minimizing rejection reactions, are particularly at risk of being infected by multi-resistant pathogens.

Worldwide, methicillin-resistant *Staphylococcus aureus* (MRSA) strains cause most infections of the skin and soft parts contracted in hospitals or nursing homes. Frequently, a sceptic course occurs, which is rated to be particularly critical. Since MRSA is not only resistant to the penicillin methicillin, but also to most other antibiotics routinely administered, therapy here is done using so-called reserve antibiotics. Nevertheless, recovery frequently is very time-consuming and difficult—if successful at all. Apart from the methicillin-resistant *Staphylococcus aureus*, there are also strains resistant to other antibiotics, such as, for example, vancomycin. Different types of bacteria, such as, for example, enterococci, pneumococci, *pseudomonas aeruginosa, campylobacter*, EHEC and others, exhibit multiple resistances and consequently are also considered to be problematic germs.

The transmission of MRP takes place either by direct contact of an MRP carrier, for example when using the same bathroom as an MRP carrier, or by treating doctors and nursing staff when neglecting to hygienic measures, in particular strict hand hygiene.

Specific hygiene measures are to be kept in order to minimize the danger of further spreading MRP. Treating doctors and nursing staff wear coats, masks and gloves and thoroughly perform hygienic disinfection of their hands. The patients are to be accommodated in single rooms.

However, in order to take and realize these measures, it is necessitated to recognize the MRP carrier status of a patient already when admitting same to a health institution. It may be advisable here to routinely screen every new patient admitted for MRP. This examination represents an important preventive measure of minimizing and, in the best case, preventing nosocomial infections with multi-resistant pathogens.

In clinical microbiology, examination materials (such as smear test swabs) which carry human-pathogenic germs are spread onto suitable universal and selective media or injected into liquid nutrient broths. After a certain incubation period, colonies may be recognized in an incubator. Cell division in most bacteria takes approximately 20 minutes so that typically days, in some cases (like *Mycobacterium tuberculosis*) even weeks, may pass until a sufficiently large number of bacteria has grown. The pathogens, however, frequently grow in mixed cultures which subsequently necessitate individual colonies to be isolated so as to obtain pure cultures. These are then multiplied, subjected to microscopy and evaluated morphologically. Using different chromogenic selective media, biochemical detection reactions and special coloring, the germs are identified.

Frequently, characterization of bacteria takes place by identifying a germ-specific enzyme set using color reactions, thereby allowing their determination and classification. Cultivating and characterizing the bacteria takes—depending on the growth behavior of the respective germ—days up to several weeks, as is described in Kayser et al., Brandis et al., and Hallman et al.

Subsequently, an antibiogram is obtained by placing selected, maybe different antibiotics disks on solid nutrient media, like those made of agar, onto which the bacteria have been spread before. Growth inhibition zones on the agar indicate whether and how sensitively the germs react to the corresponding antibiotic of the disks. Usually, an 18 to 24-hour incubation is necessitated here, which, however, may also take considerably longer with certain, mostly demanding pathogens due to slow growth. For a healing process, this may mean that a valuable amount of time elapses until a therapy may be adapted correspondingly. In other words, the antibiotics diffuse into the agar during the 18 to 24-hour incubation. If the pathogen reacts sensitively to an antibiotic, the result will be an inhibition zone around the disk applied.

As an alternative to the time-consuming conventional microbiological cultivation of the pathogens, specific deoxyribonucleic acid (DNA) sequences of multi-resistant *Staphylococcus aureus* pathogens may also be identified by means of a polymerase chain reaction (PCR). A target sequence to be identified may, for example, be the SCCmec gene. Identifying these pathogen-specific target sequences is mostly done using the classical polymerase chain reaction with corresponding primer sequences. When the DNA sequence which is complementary to the primers is present, it is multiplied. By an interaction of the DNA and the fluorescence dye, like SYBR Green I, the reaction becomes visible and measureable. The more double-strand DNA, the stronger the fluorescence signal.

Alternatively, there are also identifying methods in which identifying the bacteria DNA takes place by hybridizing using fluorescence-labeled target sequences. The Robert- Koch Institute recommends using a nasal/throat smear of the patient as a smear test material. The sensitivity of the MRSA-DNA identification is roughly 95%, specificity 97-99%. Thus, the molecular-biological MRSA direct identification is highly germ-specific and takes about 2-3 hours. However, it is of disadvantage that the molecular-biological identification is, on average, roughly 10 times as expensive as conventional methods and, for practical and organizational reasons, is analyzed only with a time offset after having collected several patient samples concerning the same problem. As experience has shown, this may take place on the next day, but may also take up to several days after having taken the sample. The consequence is that, when admitting the patient to the health institution, there is no result regarding the MRP carrier status and, consequently, it cannot be decided upon at that time whether the patient needs to be isolated or not.

The PCR-based identification is not suitable when checking the therapy course, since the DNA of non-viable bacteria is also identified. A number of living germs or a decrease in the number of living germs, which hints at healing, cannot be detected. Furthermore, this test cannot be used for on-site recognition and is comparably expensive, as is described in Hoffelder et al., Reischl et al., and Warren et al.

Creating a culture for making an antibiogram usually takes place in parallel to performing the molecular-biological examination and takes—depending on the growth behavior of the pathogen—at least one day. In addition, this method may only be performed in special laboratories using high apparatus complexity and done by qualified specialists, thereby making it unsuitable for a quick "bed-side" analysis.

In contrast to PCR methods, there are also antibody-based identification methods for multi-resistant pathogens of which some will be discussed below briefly.

Apart from molecular-biological MRSA screening, bacteriophage-based technologies are also employed. Bacteriophages are viruses which infest bacteria specifically, introduce phage DNA into the host cell, the MRP, use their replication machinery in order to have their virus genome transcribed and have their own proteins produced after translation. The phages multiply within the cell and are set free after cell lysis, i.e. the cell membrane resolving after the cell has died. The proteins produced by the phages may be identified using labeled antibodies and thus allow a specific pathogen identification. This method is also referred to as antibody-based identification method. With this method, advantage is taken from the fact that the multiplication of bacteriophages is considerably faster than that of the bacteria cells themselves, as is described in www.microphage.com A further strategy for specific MRSA identification is the so-called Q-MAP test, as is described, for example, in www.pcds-gmbh.de. Here, antibodies directed against bacteria-specific antigens are used, which are presented, i.e. arranged, on the surface of the pathogens. The antibodies are bound to magnetic nanoparticles and are incubated with/using the respective sample. When there is an antigen-antibody reaction, micro-precipitates form. These immune complexes may be detected metrologically by a Q-MAP system.

Basically, antibody-based identification strategies are—similarly to the molecular-biological approach—highly specific. However, gaining antibodies is complicated and entails comparatively high manufacturing costs. Since they are proteins and sensitive to temperature, transport and storage necessitate specific conditions. Storage stability is also limited. Reproducibility when manufacturing antibodies in a constant high quality within the individual batches may become problematic, which in turn may result in bottlenecks in the availability.

Creating a culture for obtaining an antibiogram usually takes place in parallel to performing the molecular-biological examination and takes, depending on the growth behavior of the pathogen, at least one day. This means that the specific pathogen identification is only suitable for universal entry screening to a limited extent. Since, in PCR identification, the DNA of non-living pathogens is also detected, this form of identification is not suitable for therapy control, which describes a concentration of living pathogens, for example.

At present, in the routine of health institutions, examinations for recognizing multi-resistant pathogens are done only in suspicious patients. The identification methods are either very time-consuming (microbiological-cultural identification) or very expensive and specific (molecular-biological or antibody-based identification).

Consequently, a quick test for MRP identification which allows a rapid entry examination of patients as to multi-resistant pathogens would be desirable so as to minimize considerably the risk of transmitting the pathogens to other humans and patients.

Consequently, the object underlying the present invention is providing a method and a device implementing the method, allowing multi-resistant pathogens in a sample to be identified at low time requirements.

SUMMARY OF THE INVENTION

In accordance with an embodiment, a method for detecting resistant germs in a sample may have the steps of: contacting the sample by a sample carrier which has an agent for killing different germs; introducing the sample carrier in analyzing means; detecting light emissions from the sample carrier by the analyzing means; and outputting an indication by the analyzing means indicating that the sample contains at least one germ resistant to the agent for killing different germs, if the light emission exceeds a threshold value; and outputting an indication by the analyzing means indicating that the sample does not contain germs resistant to the agent for killing different germs, if the light emission does not exceed the threshold value.

In accordance with another embodiment, a method for identifying living multi-resistant germs in a sample may have the steps of: contacting the sample by a sample carrier which has an agent for killing different germs; introducing the sample carrier into analyzing means; detecting light emissions of the living multi-resistant germs from the sample carrier by the analyzing means; and outputting an indication by the analyzing means indicating that the sample contains at least one multi-resistant germ resistant to the agent for killing different germs, if the light emission exceeds a threshold value and the at least one multi-resistant germ is thus identified in a germ-unspecific manner; or outputting an indication by the analyzing means indicating that the sample does not contain multi-resistant germs resistant to the agent for killing different germs, if the light emission does not exceed the threshold value.

In accordance with another embodiment, a device for detecting resistant germs in a sample may have: a sample carrier which has an agent for killing different germs; analyzing means configured to detect light emissions by the sample carrier; wherein the analyzing means is configured to output an indication indicating that the sample contains at least one germ resistant to the agent for killing different germs, if the light emission exceeds a threshold value; and to output an indication indicating that the sample does not contain germs resistant to the agent for killing different germs, if the light emission does not exceed the threshold value.

In accordance with still another embodiment, a device for identifying living multi-resistant germs in a sample may have: a sample carrier which has an agent for killing different germs; analyzing means configured to detect light emissions of the living multi-resistant germs from the sample carrier; wherein the analyzing means is configured to output an indication indicating that the sample contains at least one multi-resistant germ resistant to the agent for killing different germs, if the light emission exceeds a threshold value and multi-resistant germs are thus identified in a germ-unspecific manner; or to output an indication indicating that the sample does not contain multi-resistant germs resistant to the agent for killing different germs, if the light emission does not exceed the threshold values.

The central idea of the present invention is having recognized that a method examining a sample having an entirety of germs as to the presence of germs resistant to a plurality of antibiotics or antimycotics, irrespective of the bacteria or fungus strain, may provide a reliable and quick statement as to a presence of multi-resistant pathogens in the sample of the patient, while dispensing with cultivation steps. In accordance with embodiments, a presence of a small number of multi-resistant pathogens is indicated already by means of implementing the method in an apparatus having a highly sensitive detector such that further acceleration of the evaluation is possible.

Embodiments of the present invention provide a method for detecting resistant germs in a sample in which, in a first step, the sample is contacted by a sample carrier which comprises an agent for killing different germs. In a second step, the sample carrier is introduced into analyzing means. In a third step, light emissions from the sample carriers are detected by the analyzing means. In a fourth step, an indication is output by the analyzing means indicating that the sample contains at least one germ resistant to the agent for killing different germs, if the light emission exceeds a threshold value, or an indication is output indicating that the sample does not contain any germs resistant to the agent for killing different germs, if the light emission does not exceed the threshold value.

It is of advantage with this embodiment that detecting germs resistant to the agent for killing different germs, irrespective of their classification, like type or strain of the germ, allows making a statement as to a presence of multi-resistant pathogens in general and, thus, a potentially increased risk of infection or requirement of special measures, like accommodating the patient in a single room or complying with special hygiene requirements, without preparing the sample over a long time.

Further embodiments of the present invention provide a method in which the sample body is heated so that a sample at or in the sample carrier is also heated and subjected to incubation conditions which accelerate multiplication of germs in the sample.

It is of advantage with this embodiment that, based on an accelerated multiplication of the germs, a statement as to a presence of germs resistant to the agent for killing different germs may be made more quickly.

Further embodiments of the present invention provide a method in which a colorant is contacted by the sample such as the colorant penetrates into germs having intact cell membranes and marks these in color.

It is of advantage with this embodiment that a color differentiation allows an improved, i.e. earlier recognition of resistant germs. In addition, a measure of colorant absorbed by the pathogens may be an indicator of an amount of pathogens in the sample and allow making a statement as to a healing process.

Further embodiments provide a method in which the colorant comprises a dye activated by metabolic products of living germs so that recognizing resistant germs becomes possible based on dye recognition and cell activity, i.e. of the metabolic product.

It is of advantage with this embodiment that recognizing the metabolic products of resistant germs may leave the resistant germs unchanged so that the germs may be available for subsequent examinations.

Further embodiments of the present invention provide a device for performing one of the methods described above.

If the device is, for example, a mobile apparatus, it may be suitable for tasks in varying locations, like patient registration in a hospital, so that an examination result may be present already before the patient is allocated to a ward.

Further embodiments of the present invention provide a device comprising analyzing means having a photo multiplexer or a single-photon detector in order to detect light emission from the sample.

It is of advantage with this embodiment that a highly sensitive detection of light emission may result in a further accelerated recognition of resistant germs.

Further embodiments of the present invention provide a device comprising illuminating means for illuminating the sample body and for exciting a dye of a colorant to emit light so that light emission of the sample body is based on the illumination by the illuminating means.

Further embodiments provide a device comprising a container in which a dye is arranged, like a tank, for example.

It is of advantage with this embodiment that adding colorants may take place within the, maybe sealed, device and user intervention may be dispensed with.

BRIEF DESCRIPTION OF THE DRAWINGS

Embodiments of the present invention will be detailed subsequently referring to the appended drawings, in which.

DETAILED DESCRIPTION OF THE INVENTION

Before discussing below in greater detail embodiments of the present invention referring to the drawings, it is pointed out that, in the different figures, identical elements, objects and/or structures or those of equal function or equal effect are provided with same reference numerals so that the description of these elements illustrated in different embodiments is mutually exchangeable or mutually applicable.

Figure 1:
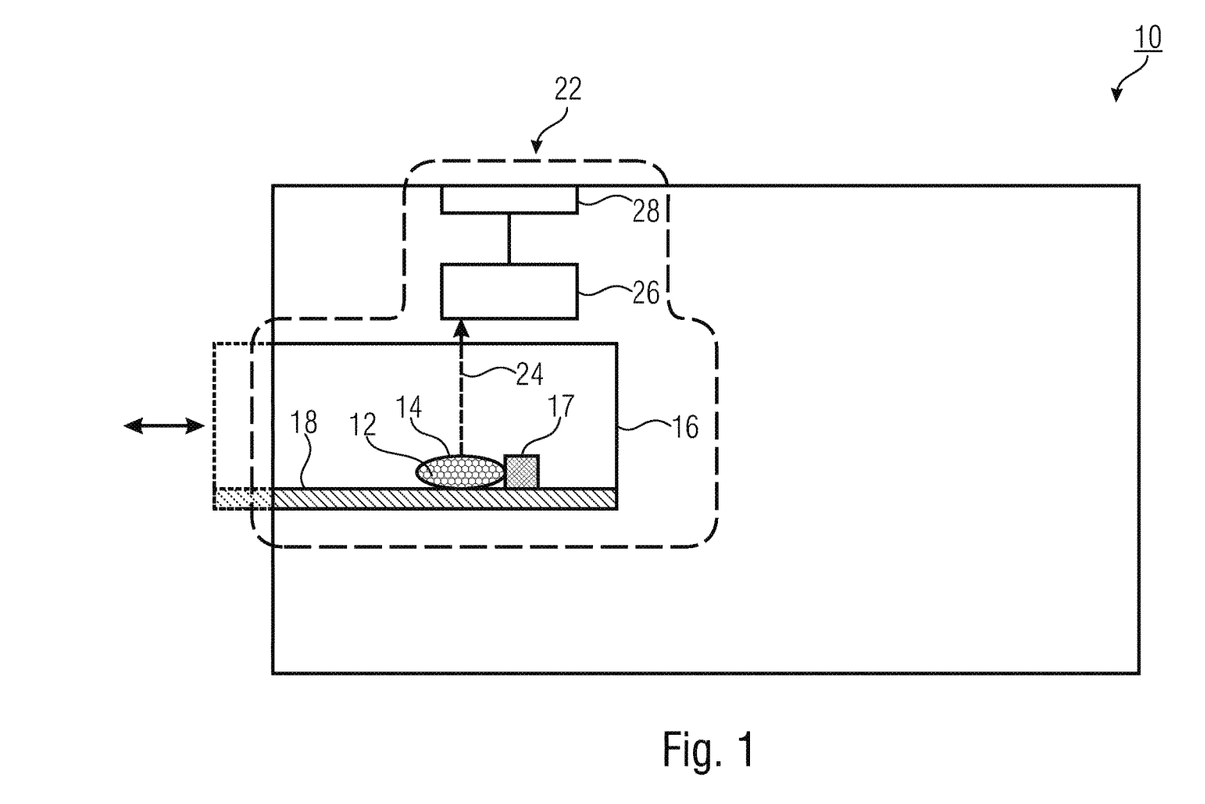
FIG. 1 shows a schematic block circuit diagram of a device for detecting resistant germs in a sample.

FIG. 1 shows a schematic block circuit diagram of a for detecting resistant germs 12 in a sample 14. The resistant germs 12 are illustrated in the sample 14 as dots. The device 10 is connected to a sample carrier 16 which comprises a nutrient medium 17 and an agent 18 for killing different germs. The sample 14, for example a nasal/throat smear of a patient, is contacted by the agent 18. The sample 14 may be an untreated patient sample, for example a sample taken directly from a patient, for example by means of a smear, and is arranged in or at the sample body 16. Alternatively, the sample 14 may also be pre-treated, for example by contacting the sample 14 by the nutrient medium 17.

In other words, the agent 18 acts on germs in the sample 14 and, depending on the activity of the agent 18, kills germs and/or pathogens in the sample 14 which are not resistant to the agent 18. Germs 12 which continue to do metabolic processes may be referred to as resistant to the agent 18. In other words, the resistant or multi-resistant germs 12 may be bacteria surviving an antibiotics mix.

The agent 18 may be an antibiotic, a combination of several antibiotics, an antimycotic, a mixture or a combination of several antimycotics or a mixture of one or several antibiotics and antimycotics. The agent 18 may thus be an individual combination of active substances, the activity of which towards germs in the sample 14 is to be tested. The active substances may each be suitable for killing germs of a type or a strain so that germs resistant to the agent 18 are resistant to two or more active substances and may be referred to as multi-resistant. The agent 18 may be a solid, a gas or a liquid. The nutrient medium 17 is configured to provide a nutrient for the germs in the sample 14 so as to allow growth and cell division thereof. The nutrient medium 17 may, for example, be agar or a nutrient broth. The germs may be bacteria or fungal pathogens.

The device 10 includes analyzing means 22 configured to detect light emission 24 from the sample carrier 16. The sample carrier may be transparent completely or partly or be implemented to be partially transparent at least for a wavelength range of light emissions 24 so that the light emission 24, when originating from the sample 14, may, at least partly, penetrate a material from which the sample carrier 16 is formed and reach the analyzing means 22.

The analyzing means 22 comprises detecting means 26 configured to receive the light emissions 24. Additionally, the analyzing means 22 comprises display means 28 configured to indicate whether light emissions 24 have been received by the detecting means 26. In other words, the analyzing means 22 is configured to detect the light emissions 24 when multi-resistant germs 12 are arranged in the sample body. Alternatively, the detector 26 does not detect light emissions 24 when no multi-resistant germs 24 are arranged in the sample 14, for example.

The light emissions 24 may, for example, result from phosphorescence, fluorescence or luminescence or a mixture thereof in germs of the sample 14 or be caused by factors which the germs of the sample 14 produce and emit. When all the non-resistant germs are killed by the agent 18, it may be concluded from the light emission 24 received that the sample 14 comprises germs 12 resistant to the agent 18. When the agent 18 is configured to kill various, different germs, the device 10 is configured to indicate, using the analyzing means 22, the presence of multi-resistant germs 12 in the sample 14. Light emission may be based on the implementation of an evaluating or identifying strategy. Various identifying strategies possible will be discussed further below.

Alternatively or additionally, the analyzing means 22 may be configured to output an indication that the sample does not contain germs resistant to the agent 18 for killing different germs. The analyzing means 22 may, for example, be configured to compare a quantity of light emission 24 received by the detector 26 to a threshold value. When higher a measure of light emission 24 is received by the detector 26 than is indicated in the threshold value, a corresponding indication may be output on the display means 28. Alternatively or additionally, the display means 28 may indicate the fact that no germs resistant to the agent 18 are contained in the sample 14 until the extent of light emission 24 exceeds the threshold value. A threshold value may, for example, compensate reception of environmental light (error light) at the detector 26, where the detector 26 receives light emission not originating from the sample 14.

The display means 28 may, for example, be a display, monitor, status light or status LED or any other means for illustrating information. Alternatively or additionally, the indication output by the display means 28 may also be an acoustic or haptic (for example a movement or vibration) signal.

The detector 26 may, for example, include a photo multiplexer or a single-photon detector configured to detect the light emission 24 already at an extent of one or a few photons. In this case, the threshold value may, for example, exhibit a value of 0. In other words, the single-photon detector allows a high-resolution measurement.

The device 10 may, for example, be used such that the sample 14 is contacted by the sample carrier 16. The sample carrier 16 may be a cuvette, another container or any other body using which or in which the sample 14 may be contacted by the sample carrier 16. The sample may, for example, be contacted by the sample carrier 16 using an induction process. The sample carrier 16 is introduced in the device 10 or analyzing means 22. This may, for example, take place by a plug or screw process, a clamping process or another method for connecting the sample carrier 16 to the analyzing means 22 such that the sample body 16 is removable and/or replaceable relative to the device 10. Alternatively, the sample body 16 may also be connected to the device 10 fixedly.

When admitting a patient, for example, the device 10, by means of a quick test, allows obtaining a hint as to whether isolation and/or admission to a quarantine ward is necessitated for the patient from whom the sample 14 originates.

It is of advantage that pre-treatment of the patient sample, for example by cultivating the pathogens contained therein and subsequently isolating germs for cultivating pure cultures of germs, using which subsequently an antibiogram is made by spreading the germs onto a solid nutrient medium (agar) and subsequently applying antibiotics plates, may be dispensed with.

In addition, sample preparation for destroying cell membranes for obtaining the DNA strands, as is, for example necessitated for PCR, may be omitted. In other words, a complete, untreated patient sample may be input into the device or the test procedure.

At this time, determination of a type, kind or strain of the multi-resistant germs 12 may be dispensed with for concluding such measures, since some measures to be taken, like accommodation in an isolation ward and/or quarantine ward, may be independent of the precise type, kind or strain of the multi-resistant pathogen. Time-saving achieved by omitting this specific categorization of the multi-resistant germs 12, which results in an unspecific "yes/no" statement on the presence of multi-resistant germs, may allow great advantages as regards patient care and/or protection of other patients from an infection by multi-resistant germs, since the corresponding measures can be taken considerably faster. Taking the measures faster may be described to be a first time advantage. When the analyzing means 22 comprises a highly sensitive silicon photo multiplexer or a single-photon detector, a small number of, possibly even a single resistant germ 12, may be recognized in the sample 14 so that a long incubation time until a certain, maybe high number of multi-resistant germs 12 have grown in the sample 14 may be dispensed with, which may result in a second time advantage. In other words, by using a highly sensitive silicon photomultiplier, smaller concentrations of pathogens than up to now can be identified. This allows avoiding long incubation times of the methods conventional at present for a microbiological-cultural cultivation of pathogens.

In other words, the patient sample (for example a nasal-throat smear) may be inducted into a container, i.e. sample body, which may contain a universal nutrient medium and, maybe, identifying reagents. In order for only multi-resistant germs to be detected in this identification, the nutrient medium is additionally provided with a suitable antibiotics mix and, maybe, antimycotics. The container may be configured such that a smear swab charged with a sample material may be immersed and rinsed. A constriction at the closure of the measuring container which is configured for an optical detection of the measuring signal allows uniform wiping of the sampler. After introducing the sample material to be examined into the medium, the container is sealed by a lid and incubated under optimal conditions. All the pathogens not exhibiting resistance to the antibiotics used cease their metabolic activities and die. All the resistant germs will multiply under the incubation conditions.

Subsequently, multi-resistant pathogens still living are identified by a fluorescence-based reaction or color reaction. The dyes used may be in solution or also bound to particulate systems (for example micro or nanoparticles). Immobilization of the dyes to a solid phase—when the identifying strategy used provides for this—is also conceivable. The quick test may be performed in an apparatus, for example in the form of a handheld apparatus, which is heatable, allows shaking the sample appropriately and is implemented with elements for a spectroscopic examination of the sample.

The method performed may also be referred to as an MRP test or quick test for on-site recognition of multi-resistant pathogens. Compared to identifying methods used at present, among which are mainly microbiological cultural cultivation and PCR, the MRP test may also be performed by staff, for example nurses, etc. not trained specifically for such tests, which allows high availability of the tests. Highly specific identifying methods are usually performed in specially equipped laboratories which are frequently located at a different location than the respective medical practice and/or the respective hospital and the patients to be examined. In addition, an error rate of the test can be reduced, which, despite the untrained staff, allows a reliable recognition of multi-resistant pathogens. Since, when implementing the device as a handheld apparatus, stationary laboratory equipment may also be dispensed with, the MRP test may be implemented in a cheaper and smaller manner and is able to indicate in a considerably shorter time whether there are multi-resistant pathogens. Alternatively, the device 10 may also be implemented to be a stationary apparatus in order to perform several tests like a quick test and additionally a test for typifying MRP pathogens, for example.

In other words, applying the MRP quick test for identifying multi-resistant pathogens or for checking on the therapy course may take place in nearly every functional position of the medical area, like a hospital or a medical specialists practice. Application thereof in other medical fields and in other regions of everyday life, for example in food control, is also conceivable. In the field of medical applications, dermatological analyzing methods of fungi, bacteria and other germs on the skin are a further field of application. The device 10 may be implemented as a handheld apparatus and be used for on-site diagnostics. The device 10 may be implemented such that it is easy to handle and cheap in manufacturing. Another advantage is that multi-resistant pathogens may be identified in a germ-unspecific manner and identification is not limited to a single species. The presence of MRSA-specific DNA sequences, like, for example, the SCCmec gene, is identified by means of PCR performed at present. Thus, this test is highly germ-specific and takes approximately 2.5 hours. The test is comparatively expensive and not suitable for on-site recognition, as is described in Hoffelder et al. and Reischl et al.

In addition, in existing tests, not all of the bacteria or fungal pathogens having gained multi-resistances can be detected, the presence of which would necessitate isolation of the patient for the prevention of contamination. An individual composition of the agent 18, maybe varying over time, in contrast, allows any composition of active substances which are aimed at killing nearly any germ. When a germ is not killed by such an agent, new, unknown or rare multi-resistant pathogens may also be identified.

The method implemented by the device 10 allows parallel performance of several tests. The sample material may be introduced in different sample containers, each containing various antibiotics in the nutrient medium, in an MRP test system with several analyzing means or in several devices such that the antibiotics suitable for treatment, i.e. those killing a majority of or all the germs, may be determined by the quick test. Thus, various antibiotics and/or antimycotics each may be arranged in the sample bodies. Where certain germs die, a corresponding therapy option may be concluded. Due to the time factor, this may have a positive effect on the therapy course of the infection since several tests performed in parallel maintain the time advantages of the quick test. This means that determination of the multi-resistant germ may also take place indirectly by performing several quick tests in parallel, by examining which active substance or antibiotics and/or antimycotics mix kills all or nearly all of the germs. The analyzing means 22 may be configured to output one or several possible types of pathogens.

In other words, the device 10 may be used in a quick test for identifying MRP in an entry examination. This test can minimize the risk of transmitting the pathogens to other patients considerably.

Alternative embodiments exhibit devices in which the analyzing means 22 is configured to represent a measure of light emission 24, which may be a measure of a concentration or an amount of multi-resistant germs 12 in the sample 14, in a relative, scaled or absolute manner such that multiplication or reduction of the multi-resistant germs 12 in the sample body 16 is, for example, represented by means of a display value in the display means 28 varying over different points in time.

Although the detector 26 has been described as comprising a photomultiplier or single-photon detector, other detector elements, for example comprising miniaturized silicon devices, may also be arranged alternatively or additionally. Silicon devices may exhibit a smaller energy consumption and at the same time be cheap. In addition, the detector 26 may also be implemented to be a receiver of a confocal microscope. Using an element which is able to identify even single photons may allow the identifying method to be shortened to a few hours. (A test time may, for example, take less than 5 hours, less than 3 hours, or less than 1 hour). A cultivation over several hours for multiplying the sample quantities or germs contained therein may then become unnecessary.

Although the agent 18 and the nutrient medium 17 are illustrated as separate objects, the nutrient medium 17 and/or the agent 18 may be liquid or gel-like substances which are mixed heterogeneously or homogeneously. Mixing may, for example, take place by a shaking or stirring process. Alternatively, the agent 18 may also be dissolved in the nutrient medium 17 or vice versa such that the agent 18 or the nutrient medium 17 is a dispersion or suspension in the respective other constituent part. Additionally, the sample 14 may be dissolved in the agent 18 and/or the nutrient medium 17 or be bound to the agent 18 and/or the nutrient medium 17 in a heterogeneous or homogeneous manner, for example when the sample 14 is inducted or stirred into the agent 18 and/or the nutrient medium 17 when the agent 18 and/or the nutrient medium 17 is/are liquid.

Figure 2:
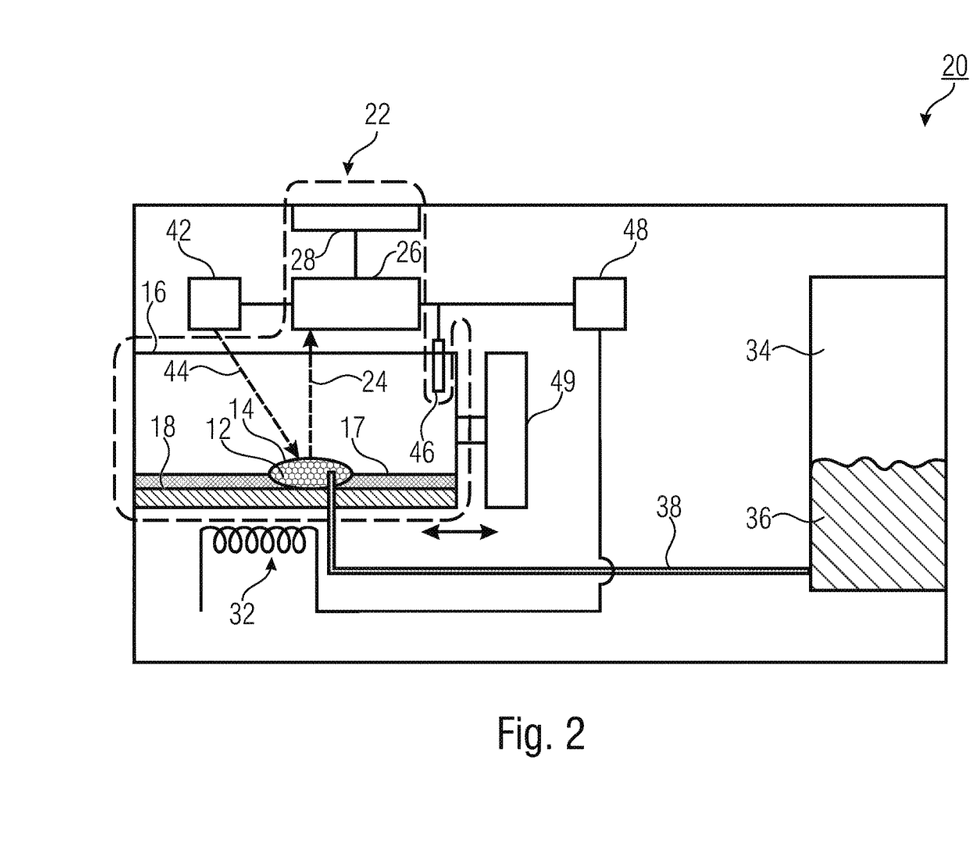
FIG. 2 is a schematic block circuit diagram of another device for detecting the resistant germs in a sample, with a range of functions enlarged compared to the device of FIG. 1.

FIG. 2 shows a schematic block circuit diagram of another device 20 for detecting the resistant germs 12 in the sample 14. Compared to the device 10, the device 20 exhibits an enlarged range of functions.

The device 20 includes a container 34 configured to contain a colorant 36 and to contact the colorant 36 and the sample 14 via a feed line 38. The colorant 36 is configured to completely or partly penetrate in and thus mark the resistant germs 12 or to exhibit a color reaction based on a metabolic product of the resistant germs 12 such that light emission 24 is influenced by the dye or colorant 36. In other words, resistant germs 12 may be marked for direct identification or reaction products of the substances of the resistant (living) germs 12 in the sample carrier may be made measureable such that indirect identification of the resistant germs 12 is allowed. The colorant 36 may, for example, comprise fluorescence or phosphorescence substances.

Additionally, the device 20 comprises illuminating means 42 configured to emit illumination radiation 44 such that the illumination radiation 44 illuminates the sample 14 in or at the sample body 16. The illumination radiation 44 may be electromagnetic radiation and may, for example, be configured to excite fluorescence or phosphorescence of a dye of the colorant 36. The sample body 16 is at least partly transparent for the illumination radiation 44 and light emission 24 such that the illumination radiation may penetrate, at least partly, the sample body 16 in a direction towards the sample 14 and light emission 24 may penetrate the sample body in a direction from the sample 14 to the detector 26.

An characteristic or implementation of the colorant 36 may be based on an evaluating strategy of the test method or be dependent thereon. Various evaluating strategies will be discussed below. The colorant 38 may, for example, be configured to penetrate through cell membranes of germs having survived contact with the agent 18 and thus mark the living, i.e. resistant, germs 12 in the sample carrier 16. Alternatively, it is also feasible for the colorant 36 to indicate a change in color or a change in light based on a metabolic product of the resistant germs 12 by inducing or catalyzing the color reaction or light change reaction, like, for example, fluorescence, phosphorescence or luminescence, by a metabolic product of the multi-resistant germs 12 such that a dye, like a fluorescent or phosphorescent substance, is activated or released. In other words, the bacterium itself or products/factors formed by it (proteins) can be identified.

The colorant may, for example, be configured to mark the resistant germs 12 based on a membrane integrity of the resistant germs 12 and thus allow identification.

One potential strategy includes marking living germs in colors. Coloring may, for example, be coloring the nucleic acids in the cells such that evaluation of light emission 24 may take place based on a quantity or intensity of light emission 24 relative to a wavelength of coloring.

Additionally, a further possible strategy includes marking in different colors of living and dead germs, for example by contacting two dyes or colorants of different colors with the sample 14. A first colorant, for example a dye of green fluorescence, is configured to penetrate intact and defect cell membranes, i.e. cell membranes of living and dead germs. In other words, living and dead germs are marked by a first color (green). A second colorant, for example a dye of red fluorescence, is configured to pass only defect membranes, i.e. membranes of dead germs. In other words, dead germs are marked by a second color (red). When the two colorants are used in a certain ratio, living germs may, for example, appear green, whereas dead germs appear red. With a color differentiation between living and dead germs, evaluation by the evaluating means 22 may be done using optical criteria, for example using a fluorescent reader as is described, for example, in Monis et al., Wlodkowic et al., and Wojcik et al. The certain ratio may depend on the implementation or sensitivity, for example color sensitivity, of the analyzing means and/or on a color contrast desired.

In accordance with another strategy, identification of living germs may be done by measuring an activity of cellular esterase. The sample 14 may be contacted by two different fluorescent colorants, for example by adding the fluorescent dyes to the nutrient medium 17 or guiding same in or at the sample body 16 via the feed line 38. A first dye may, for example, be an acetomethyl-(AM-) ester-based substrate, like Calcein-AM, 2',7'-bis-(2-carboxyethyl)-5-(and-6)-carboxyfluorescein (BCECF)-AM, ChemChrome V6 (CV6) or fluorescein-diacetate FDA. A second dye may, for example, be a nucleic acid-coloring fluorophore, like ethidium-homodimer-I or III or CSE/2 in the colorant 36.

Acetomethyl-ester-based substrates are usually membrane-penetrating, i.e. the substrates are absorbed by the resistant germs 12, and are non-fluorescent. Within the germ, the acetomethyl residues are split off enzymatically by unspecific esterases. This results in fluorescence of the remaining fluorophore. The substance, i.e. fluorophore, remains within the cell. In other words, acetomethyl residues may be bound to a fluorophore, like fluorescein, via ester bonding. The fluorophore alone frequently is not membrane-penetrating, but may pass the cell membrane by introducing the AM residues. Esterases which split the ester bonds of the modified fluorophore are located in the cytoplasm of the cells. What remains is the fluorophore with no AM—in this form, it is fluorescent and no longer membrane-penetrating, i.e. may no longer leave the cell. In fluorescein, the cell, when being excited correspondingly, shines green. This allows ensuring that only living cells of the germs 12 are detected, since membranes of dead germs are inactive or destroyed. By further adding a DNA-binding fluorophore, like ethidium-homodimer-I or III, which may pass only defect membranes, it is possible to mark living and dead bacteria to fluoresce differently, as is described, for example, in Decker, Leeder et al., Liminga et al., and Parthuisot et al.

Adding a second colorant which marks dead bacteria or germs may increase resolution of the analyzing method.

In accordance with another evaluating strategy, multi-resistant germs 12 may be identified using proteins formed by the resistant germs 12. The exoenzyme DNAse may, for example, be suitable as a virulence factor which may be a measure of a health danger and/or risk of infection, when a sample is analyzed as to a presence of multi-resistant germs of the *Staphylococcus aureus* type. The enzyme DNAse is formed (exprimed) by the living germ and released to its surroundings, for example to the nutrient medium 17, the agent 18 and/or the dye 36. Identifying DNAse may be done by adding or contacting by the sample 14 short labeled DNA fragments, for example comprising a number between 20 and 200, between 30 and 150 or between 40 and 60 pairs of bases, for example 50. In other words, contacting the dye is done in the surroundings to which the exoenzyme is released, like the nutrient medium 17 in which the germ is also to be cultivated. The labeled DNA fragments may be manufactured synthetically and may comprise a fluorescence label and a quencher.

The DNA fragments may form after hybridizing three individual strands, one unlabeled (for example consisting of 50 nucleotides) and two oligonucleotides which are complementary to the unlabeled individual strand. One of the two oligonucleotides is, for example, provided with a quencher, the other one with a fluorophore such that the fluorophore and the quencher, after hybridizing the three individual strands, are spatially so close to each another that the fluorescence will be quenched. With a reaction with the exoenzyme DNAse, the DNA is split, fluorophore and quencher may separate from each other spatially such that fluorescence is no longer suppressed and the fluorophore becomes identifiable. The quencher is configured to quench, i.e. suppress, fluorescence of the fluorophore.

The presence of DNAse results in the DNA fragment to be split such that the fluorophore is arranged on one part of the fragment and the quencher at another part. The fluorophore may be excited to fluoresce irrespective of the quencher, since the quencher is arranged on another part. In other words, the quencher, i.e. fluorescence suppressor, is split such that fluorescence is no longer suppressed at the corresponding segment. After exciting the fluorophore, for example by the illuminating means 42 and the illumination radiation 44, fluorescence may be excited in the nutrient medium where at least one multi-resistant germ 12 is located and can be detected by the detector 26. Identifying the splitting of DNA fragments is described, for example, in Eisenschmidt et al. and Ghosh et al.

Alternatively, other exoenzymes may also be identified. The enzyme hyaluronidase is exprimed and released to its environment by living resistant germs 12, for example bacteria, like *Staphylococcus aureus, Staphylococcus epidermidis, Streptococcus pyogenes*. Identifying hyaluronidase may take place by adding short labeled hyaluronic acid fragments in the environment of resistant germs 12, like the nutrient medium 17. The hyaluronic acid fragments may be provided with a quencher at one end and with a fluorophore at another end. This means that fluorescence is also quenched. When there is hyaluronidase, the fragment is split and, after corresponding excitation, fluorescence may be detected, as is described, for example, in Fudula et al. (both listed literatures) and Zhang et al.

In accordance with a further strategy, sugar breakdown in the environment of the multi-resistant germs 12 by same can be identified. The enzyme galactosidase splits lactosen to form glucose and galactose, for example. When, to D galactose, a sugar molecule which, as far as structure is concerned, differs only slightly from glucose, a fluorophore which is only fluorescent when free in solution or which changes its fluorescent characteristics, like intensity or wavelength or color, when no longer bound to D galactose is bound instead of glucose, sugar breakdown can be made visible when the enzyme galactosidase has split off the fluorophore from D galactose.

When there are multi-resistant germs 12 which produce galactosidase, for example *Staphylococcus aureus* or coliform bacteria, as well as the labeled sugar (D galactose, which is labeled by the fluorophore) in the medium, for example a mixture of sample 14, agent 18, nutrient medium 17 and/or colorant 36, sugar breakdown and, thus, the presence of multi-resistant germs 12, may be made visible when the D galactose is split off and a fluorescence signal of the fluorophore is detected by the analyzing means 22. Fluorescein which, as an acetyl fluorescein, is not fluorescent but, after hydrolysis catalyzed by the enzyme galactosidase, for splitting the sugar residue is transformed to a fluorescent product may, for example, be a suitable fluorophore, as is described, for example, in Peak et al., and Guilbault et al.

In accordance with a further identification strategy, surviving, respiratorily active resistant germs 12, i.e. converting oxygen or another respiratory gas, may also be identified using a redox sample. The sample 14 here may, for example, be contacted by a 5-cyano-2,3-ditolyl tetracolium chloride (CTC). Oxidized CTC is colorless and non-fluorescent. This substance is absorbed into the cell of the living multi-resistant germ 12. Within the cell, it functions in the electron transport chain (respiratory chain) as an artificial, i.e. further electron acceptor and is reduced in the respiratory process during the respiratory chain. Reduced CTC is fluorescent, precipitates as an insoluble CTC formazan and accumulates in living cells of the multi-resistant germs 12, as is described in Rodriguez et al.

The various identifying strategies illustrated are to be understood to be only exemplary. In principle, other identifying strategies for identifying multi-resistant germs 12 may also be applied. The different identifying strategies may be combined with one another such that a specific exciter identification becomes possible using the exciter-specific enzyme set thereof, for example by sequentially performing several tests or by performing several tests in parallel in several devices.

The strategies described for recognizing multi-resistant germs 12 are based on identifying metabolically active germs or bacteria. Thus, these methods are also suitable for being employed when monitoring the therapy progress. This may, for example, take place such that methods for detecting multi-resistant germs 12 are performed in different time intervals of, for example, hours, days or weeks, and a concentration of multi-resistant germs 12 is indicated in the respective sample 14. Furthermore, it is conceivable for the devices and methods suggested here to be used also in quick tests to discover specifically resistances in exciters already isolated and identified. Changes, like new resistances in pathogens identified, may also be determined in this way.

The device 20 includes a heating element 32 configured to heat the sample body 16 and, thus, the sample 14 and the resistant germs 12 to a constant or varying temperature. The heating element 32 is configured to heat the sample body 16 to a temperature in a range between 25° Celsius and 45° Celsius. Heating may, for example, be used to reproduce optimum temperatures, i.e. adapted to the body of the patient or the environment from which the sample has been taken, like 37° Celsius, in order to allow optimum multiplication of the germs 12. Alternatively, the heating element may be configured to heat the sample body to a germ-specific temperature when the sample 14 is to be examined for a certain pathogen.

Heating may result in further shortening the test time and, thus, a third time advantage. Alternative embodiments show heating elements configured to heat the sample body to a temperature in a range between 30° Celsius and 42° Celsius or between 35° Celsius and 40° Celsius. This allows incubation or heating to the temperature for the identification reaction in the device 20 directly.

Alternatively or additionally, the heating element 32 may be configured to heat the sample body 16 to a temperature which is greater than 70° Celsius, greater than 100° Celsius or greater than 200° Celsius, in order to destroy the sample 14 and/or disinfect the sample or the sample body 16.

Additionally, the device 20 comprises moving means 49 for shaking the sample body 16. The means 49 may, for example, be a piezo or electric motor. Shaking the sample body 16 may allow mixing the nutrient 17, the agent 18 and/or the colorant 38 and the sample 14 such that the result, completely or partly, is a mixture of substances which is analyzed as a whole by the analyzing means 22. A mixture of substances allows improved action of the agent 18 on the germs of the sample 14, improved nutrition of the resistant germs 12 by means of the nutrient medium 17 and more homogenous action of the colorant 36.

Alternatively, the device 20 or the sample body 16 may also be shaken manually before contacting, i.e. introducing, the sample body 16 by the device 20 or when the sample body 16 is contacted by the device 20 and the device 20 is a handheld apparatus.

The device 20 comprises an optional temperature sensor 46 configured to detect the temperature in the sample body 16. In addition, the device 20 comprises optional calculating means 48 configured to detect the temperature detected by the temperature sensor 46 and drive the heating element 32 such that a temperature control loop may be implemented. Of advantage with a temperature control loop is that a temperature in the sample body varies in a predetermined manner and may be re-regulated, for example when different amounts of sample material, i.e. differently large samples 14, in different sample bodies 16 are introduced into the device 20 using different tests performed.

Alternative embodiments show devices comprising one or several additional containers for liquids and/or gases, and feed lines and configured to contact liquids and/or gases by the sample. Thus, gassing the sample and, thus, the germs by the respective gas, like oxygen, nitrogen and/or carbon dioxide, may, for example, take place to further accelerate incubation of the germs. Furthermore, air humidity in a range between 20% and 100%, 30% and 90% or 40% and 80%, for example, around the sample may be set using the liquid, for example water, in order to accelerate incubation of the germs.

In addition, alternative embodiments comprise sensors for measuring the humidity, for example a hygrometer, or measuring a gas concentration, for example a gas spectrometer, in order to detect air humidity and/or the gas concentration in the environment of the sample. The sensors may be connected to a processor means or a calculating means 48 in order to enable a control loop for controlling air humidity or gas concentration.

Although, in the above expositions, the illuminating means 42 has been described to be part of the device 20, the illuminating means 42 may also be part of the analyzing means 22, for example when the analyzing means comprises a confocal microscope for detecting light emission 24.

Alternatively or additionally, it is also conceivable for the device 20 to be configured to be contacted by another sample carrier. A reference sample may be arranged in or at the further sample carrier. The reference sample may, for example, be configured such that it does not comprise resistant germs 12. The reference sample may be contacted by the nutrient medium 17, the agent 18 and/or the colorant 36. The analyzing means 22 may be configured to analyze the sample 14 and the reference sample. The colorant may be contacted by the sample 14 and the reference sample at a time when the agent 18 has not killed any or all the living germs in the sample or in the reference sample, i.e. non-resistant germs and the metabolic products thereof are also marked and contribute to light emission 24. Based on the agent 18, light emission in the reference sample may decrease stronger than in the sample 14 when the non-resistant germs die and only germs (still) living contribute to further light emission. Light emission of the reference sample may thus represent a varying, dynamic threshold value. When light emission 24 and light emission of the reference sample differ increasingly with an increasing duration in which the agent 18 is contacted by the sample 14 and the reference sample, this may be an indication of a presence of resistant germs 12 in the sample 14. This may result in a further time advantage when waiting for the onset of an action of the agent 18 may be omitted completely or partly, until starting to analyze the sample 14.

Identifying the resistant germs may take place by comparing light emission 24 to light emission of the reference sample, when, for example, the sample 14 is incubated equally or similarly as is the reference sample and light emission 24 is greater than the light emission of the reference sample. In other words, a cuvette which contains the reference sample, may, as regards its quality, be implemented such that it basically does not differ from the sample to be analyzed, except that no multi-resistant pathogens are contained (MRP-negative sample), may be contacted as another sample body by the device 20 such that the device 20 may be configured to be contacted by two or more sample bodies at the same time or one after the other. This allows comparing light emission 24 to a dynamic threshold value which may be individual for every sample 14 to be analyzed.

In other words, the methods and devices described here aim at identifying multi-resistant pathogens in a comparatively cheap manner and within a short time so that the risk of transmitting MRP to other patients may be decreased considerably. The corresponding device may be set up such that it is suitable for quick tests, for example as a handheld apparatus, in entry examinations or patient admittance to a medical institution.

Identifying MRP may be done by measuring the enzymatic activity of proteins formed by pathogens still living (for example virulence factors, like DNAse, catalase, hyaluronidase and others, but also enzymes of the biochemical metabolism, like β-galactosidase, α-amylase and others) and/or by determining the integrity of their membranes while using fluorescence indicators or color indicators.

Figure 3A:
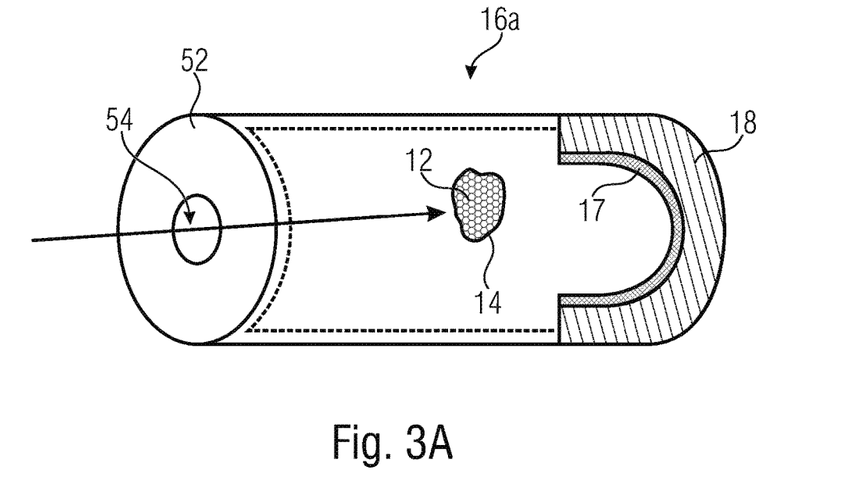
FIG. 3a shows an exemplary embodiment of a sample body implemented as an almost sealed volume.

FIG. 3a shows an exemplary embodiment of a sample body 16a implemented as a nearly closed volume. The sample body 16a comprises a closure 52 which may be removed from the remaining sample body 16a. Thus, for example after having performed a test, the sample body 16a may be cleaned and/or disinfected. A new sample 14, a new agent 18 and/or nutrient 17 may also be introduced into the sample body 16a, same may be closed by the closure 52 and a new test be performed. The closure 52 comprises an opening 54 configured to allow the sample 14 to be entered through the closure 52 so that a smear swab charged with the sample 14 may, for example, be immersed in the sample body 16a and the sample 14 be wiped onto the agent 18 and/or the nutrient material 17 or be rinsed from the colorant. Alternatively or additionally, the opening 54 may also be sealed and comprise a component permeable for feed lines or cannulas, for example for nutrient material 17 and/or colorants, like a rubber layer. Alternatively, the colorant, the nutrient 17 and/or the agent 18 may be a mixture of substances mixed among one another or a liquid such that the sample 14 is stirred or rinsed by stirring a swab in the mixture of substances or the liquid in the sample body 16a.

Alternatively, the closure 52 may also be arranged fixedly on the sample body 16a, for example when the sample body 16a is configured only for single use. The opening 54 may be closed by another closure, like a plug.

Figure 3B:
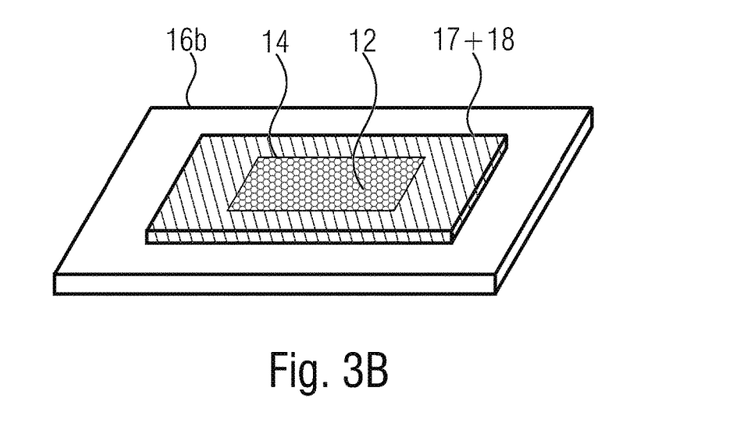
FIG. 3b shows a schematic illustration of a sample body implemented as a plate.

FIG. 3b shows a schematic illustration of a sample body 16b implemented as a plate. On a main side, i.e. a surface of the sample body 16b having a large area or the largest area, the nutrient 17 and the agent 18 for killing various germs are arranged as a mixture of substances. The sample 14 having the multi-resistant germs 12 is arranged on the mixture of substances. Implementing the sample body 16b as a plate may result in a structural size reduced compared to the sample body 16a in FIG. 3a, for example, which may also result in smaller an implementation of the device 10 or 20 of FIG. 1 or FIG. 2. The sample body 16b may, for example, be a test strip having a layer of agar as a nutrient medium 17. A plate or cover configured to prevent contamination may, for example, be arranged on the sample body 16b. Contamination may, for example, take place by the multi-resistant germs 12 entering in the sample 14 or by parts or agents, for example disinfectants or lubricants, entering in the sample. In principle, this sample body 16 may exhibit any shape.

Although, in the above embodiments, the colorant has been contacted by the sample via a feed line, it is also conceivable for the colorant as an identifying reagent including the agent for killing several germs and/or the nutrient medium to be arranged in or at the sample body, or a common agent for killing several germs or a mixture of substances including the agent for killing several germs and/or the nutrient medium.

Although some aspects have been described in the context of a device, it is clear that these aspects also represent a description of the corresponding method, such that a block or element of a device also corresponds to a respective method step or a feature of a method step. Analogously, aspects described in the context of or as a method step also represent a description of a corresponding block or detail or feature of a corresponding device.

Depending on certain implementation requirements, embodiments of the invention may be implemented in hardware or in software. The implementation can be performed using a digital storage medium, for example a floppy disk, a DVD, a Blu-Ray disc, a CD, an ROM, a PROM, an EPROM, an EEPROM or a FLASH memory, a hard drive or another magnetic or optical memory having electronically readable control signals stored thereon, which cooperate or are capable of cooperating with a programmable computer system such that the respective method is performed. Therefore, the digital storage medium may be computer-readable. Some embodiments according to the invention include a data carrier comprising electronically readable control signals which are capable of cooperating with a programmable computer system such that one of the methods described herein is performed.

Generally, embodiments of the present invention can be implemented as a computer program product with a program code, the program code being operative for performing one of the methods when the computer program product runs on a computer. The program code may, for example, be stored on a machine-readable carrier.

Other embodiments comprise the computer program for performing one of the methods described herein, wherein the computer program is stored on a machine readable carrier.

In other words, an embodiment of the inventive method is, thus, a computer program comprising a program code for performing one of the methods described herein, when the computer program runs on a computer. A further embodiment of the inventive methods is, thus, a data carrier (or a digital storage medium or a computer-readable medium) comprising, recorded thereon, the computer program for performing one of the methods described herein.

A further embodiment of the inventive method is, thus, a data stream or a sequence of signals representing the computer program for performing one of the methods described herein. The data stream or the sequence of signals may, for example, be configured to be transferred via a data communication connection, for example via the Internet.

A further embodiment comprises processing means, for example a computer, or a programmable logic device, configured to or adapted to perform one of the methods described herein.

A further embodiment comprises a computer having installed thereon the computer program for performing one of the methods described herein.

In some embodiments, a programmable logic device (for example a field-programmable gate array, FPGA) may be used to perform some or all of the functionalities of the methods described herein. In some embodiments, a field-programmable gate array may cooperate with a microprocessor in order to perform one of the methods described herein. Generally, in some embodiments, the methods are performed by any hardware apparatus. This can be a universally applicable hardware, such as a computer processor (CPU) or hardware specific for the method, such as an ASIC.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

LITERATURE

[1] Kayser F. H., K. A. Bienz, J. Eckert, R. M. Zinkernagel; Medizinische Mikrobiologie; Georg Thieme-Verlag, Stuttgart—New York (1998) 9. Auflage
[2] Brandis H., W. Köhler, H. J. Eggers, G. Pulverer; Lehrbuch der medizinischen Mikrobiologie; Gustav Fischer Verlag, Stuttgart—Jena—New York (1994) 7. Auflage
[3] Hallmann L. und F. Burkhardt, Klinische Mikrobiologie, Georg Thieme-Verlag, Stuttgart (1974) 4. Auflage
[4] Hoffelder M., A. M. Fahr, A. Turnwald-Maschler, U. Eigner; Direct detection of methicillin-resistant *Staphy-* lococcus aureus in clinical specimens by a nucleic acid-based hybridization assay; Clin Microbiol Infect (2006) 12(12): 1163-1167

[5] Reischl U. und T. Holzmann; Aktuelle Verfahren zum Nukleinsäure geschützten Direktnachweis von MRSA; J Lab Med (2008) 32(4): 253-265

[6] Warren D. K., R. S. Liao, L. R Merz, W. M. Jr. Dunne; Detection of methicillin-resistant *Staphylococcus aureus* from nasal swab specimens by a real time PCR assay; J Clin Microbiol (2004) 42(12): 5578-5581

[7] www.microphage.com

[8] www.pcds-gmbh.de

[9] Monis P. T., S. Giglio, C. P. Saint; Comparison of SYT09 and SYBR Green I for real-time polymerase chain reaction and investigation of the effect of dye concentration on amplification of DNA melting curve analysis; Anal Biochem (2005) 340: 24-34

[10] Wlodkowic D., J. Skommer, Z. Darzynkiewicz; SYTO probes in the cytometry if tumor cell death; Cytometry A (2008) 73: 496-507

[11] Wojcik K. and J. W. Dobrucki; Interaction of DNA intercalator DRAQ5, and a minor groove hinder SYTOJ7, with chromatin in live cells—influence on chromatin organization and histone-DNA interaction; Cytometry A (2008) 73: 555-562

[12] Decker E. M.; The ability of direct fluorescence-based, two-color assays to detect different physiological states of oral streptococci; Lett Appl Microbiol (2001) 33: 188-192

[13] Leeder J. S., H. M. Dosch, P. A. Harper, P. Lam, S. P. Spielberg; Fluorescence-based viability assay for studies of reactive drug intermediates; Anal Biochem (1989) 177: 364-372

[14] Liminga G., B. Jonsson, Nygren, R. Larsson; the mechanism underlying calcein-induced cytotoxicity; Eur J Phannacol (1999) 383: 321-329

[15] Parthuisot N., P. Catala, K. Lemarchand, J. Baudart, P. Lebaron; Evaluation of ChemChrome V6 for bacterial viability assessment in waters; J Appl Microbiol (2000) 89: 370-380

[16] Eisenschmidt K., T. Lanio, A. Jeltsch, A. Pingoud; A fluorimetric assay for on-line detection of DNA cleavage by restriction endonucleases; J Biotechnol (2002) 96: 185-191

[17] Ghosh S. S., P. S. Eis, K. Blumeyer, K. Fearon, D. P. Millar; Real time kinetics of restriction endonuclease cleavage monitored by fluorescence resonance energy transfer; Nucleic Acids Res (1994) Vol. 22, No. 15 3155-3159

[18] Fudala R., M. E. Mummert, Z. Gryczynski, I. Gryczynski; Fluorescence detection of hyaluronidase; J Photochem Photobiol B (2011) 104:473-477

[19] Fudala R., M. E. Mummert, Z. Gryczynski, R. Rich, J. Borejdo; Lifetime-based sensing of hyaluronidase using fluorescein labeled hyaluronic acid; J Photochem Photobiol B (2012) 106: 69-73

[20] Zhang L. S. and M. E. Mummert; Development of a fluorescent substrate to measure hyaluronidase activity; Anal Biochem (2008) 379: 80-85

[21] Peak E., I. W. Chalmers, K. F. Hoffmann; Development and validation of a quantitative, high-throughput, fluorescence-based bioassay to detect *schistosoma* viability; PLoS Negl Trop Dis (2010) 4:e759

[22] Guilbault G. G. and D. N. Kramer; Fluorimetric procedure for measuring the activity of dehydrogenasis; Anal Chem (1965) 37: 1219-1221

[23] Rodriguez G. G., D. Phipps, K. Ishiguro, H. F. Ridgway; Use of a fluorescent redox probe for direct visualization of actively respiring bacteria; Appl. Environ Micobiol (1992) 1801-1808

The invention claimed is:

1. A method for detecting living multi-resistant germs in a sample, comprising:
    contacting the sample by a sample carrier which comprises an agent for killing different germs; wherein the agent comprises a combination of antibiotics and/or antimyotics;
    introducing the sample carrier in an analyzer;
    detecting light emissions of the living multi-resistant germs from the sample carrier by the analyzer;
    wherein the light emissions result from enzymatic activity of proteins comprising DNAse and/or catalase and/or hyaluronidase formed by pathogens still living;
    outputting an indication by the analyzer indicating that the sample comprises at least one multi-resistant germ resistant to the agent for killing different germs, if the light emission exceeds a threshold value and the at least one multi-resistant germ is thus identified in a germ-unspecific manner; and
    outputting an indication by the analyzer indicating that the sample does not comprise living multi-resistant germs resistant to the agent for killing different germs, if the light emission does not exceed the threshold value.

2. The method in accordance with claim 1, wherein the sample carrier for contacting the sample by the sample carrier additionally comprises a nutrient for different germs.

3. The method in accordance with claim 1, further comprising:
    providing a colorant which marks living germs in the sample carrier or renders a metabolic product of the living germs in the sample carrier measurable, wherein providing the colorant takes place such that, in contacting the colorant by the sample, the colorant is split based on a splitting process of the colorant induced by the metabolic product of the germs and the colorant is activated; and
    contacting the colorant by the sample.

4. The method in accordance with claim 3, wherein the sample carrier for contacting the sample by the sample carrier comprises the colorant.

5. The method in accordance with claim 1, further comprising:
    providing a photomultiplier or a single-photon detector for detecting the light emission;
    illuminating the sample carrier by electromagnetic radiation on which light emission from the sample carrier is based.

6. The method in accordance with claim 1, further comprising:
    evaluating a kind or strain of the living multi-resistant germ resistant to the agent for killing different germs;
    outputting an indication by the analyzer indicating the kind or strain of the living multi-resistant germ.

7. The method in accordance with claim 1, further comprising:
    heating the sample carrier to a temperature in a range between 35° C. and 40° C. after introducing the sample carrier in the analyzer.

8. The method in accordance with claim 1, further comprising:
    shaking the sample carrier when the sample carrier is contacted by the sample.

9. A device for detecting living multi-resistant germs in a sample, comprising:
- a sample carrier which comprises an agent for killing different germs, wherein the agent comprises a combination of antibiotics and/or antimyotics; and
- an analyzer configured to detect light emissions of the living multi-resistant germs resulting from enzymatic activity of proteins comprising DNAse and/or catalase and/or hyaluronidase formed by pathogens still living;
- wherein the analyzer is configured to output an indication indicating that the sample comprises at least one multi-resistant germ resistant to the agent for killing different germs, if the light emission exceeds a threshold value and multi-resistant germs are thus identified in a germ-unspecific manner; and
- to output an indication indicating that the sample does not comprise multi-resistant germs resistant to the agent for killing different germs, if the light emission does not exceed the threshold value.

10. The device in accordance with claim 9, further comprising a container configured to comprise a colorant and release same to the sample carrier.

11. The device in accordance with claim 9, wherein the analyzer comprises a photomultiplier or a single-photon detector configured to detect light emissions from the sample carrier.

12. The device in accordance with claim 9, further comprising an illuminator configured to illuminate the sample carrier.

13. The device in accordance with claim 9, wherein the analyzer is further configured to determine a kind or strain of the living multi-resistant germ resistant to the agent for killing different germs and to output an indication indicating the kind or strain of the living multi-resistant germ.

14. The device in accordance with claim 9, further comprising a heating element configured to heat the sample carrier to a temperature in a range between 35° C. and 40° C.

15. The device in accordance with claim 9, further comprising a shaker for shaking the sample carrier.

* * * * *